US006908226B2

(12) United States Patent
Siddiqui et al.

(10) Patent No.: US 6,908,226 B2
(45) Date of Patent: Jun. 21, 2005

(54) METHOD AND APPARATUS FOR ASPIRATING LIQUID FROM A CONTAINER

(75) Inventors: Imran T. Siddiqui, Santa Clarita, CA (US); Santos E. Vargas, Miami Lakes, FL (US); Roberto Del Valle, Coral Gables, FL (US)

(73) Assignee: Beckman Coulter, Inc., Fullerton, CA (US)

( * ) Notice: Subject to any disclaimer, the term of this patent is extended or adjusted under 35 U.S.C. 154(b) by 0 days.

(21) Appl. No.: 10/360,665

(22) Filed: Feb. 7, 2003

(65) Prior Publication Data

US 2004/0156417 A1 Aug. 12, 2004

(51) Int. Cl.[7] ................................................ G01N 35/10

(52) U.S. Cl. ........................... 374/45; 374/54; 374/142; 374/183; 338/252; 73/295; 73/864.01; 422/100; 436/180

(58) Field of Search ......................... 600/549; 422/100; 73/864.01, 295; 436/180; 374/45, 54, 141, 142; 338/22 R, 28, 252, 226, 229, 256

(56) References Cited

U.S. PATENT DOCUMENTS 4,135,186 A 1/1979 Minorikawa et al.
4,276,260 A 6/1981 Drbal et al.
4,280,508 A * 7/1981 Barrada ...................... 600/549
4,341,736 A 7/1982 Drbal et al.
4,630,477 A * 12/1986 Murtland, Jr. ............... 73/295
4,896,546 A 1/1990 Cabrera et al.
5,056,363 A 10/1991 Arekapudi et al.
5,212,992 A * 5/1993 Calhoun et al. ......... 73/864.01
5,380,486 A * 1/1995 Anami ........................ 422/63
6,100,094 A * 8/2000 Tajima ........................ 436/54
6,121,049 A * 9/2000 Dorenkott et al. ............ 436/50
6,322,752 B1 * 11/2001 Siddiqui et al. ............ 422/100
6,383,144 B1 * 5/2002 Mooney et al. ............. 600/549
6,435,710 B1 * 8/2002 Fauske ........................ 374/54
6,511,478 B1 * 1/2003 Burnside et al. ............ 600/549
6,551,558 B1 * 4/2003 Mann et al. ................ 422/100

* cited by examiner

*Primary Examiner*—Diego Gutierrez
*Assistant Examiner*—Stanley J. Pruchnic, Jr.
(74) *Attorney, Agent, or Firm*—Warren W. Kurz; Mitchell E. Alter

(57) ABSTRACT

A method and apparatus for aspirating a liquid (e.g., blood) from a container uses an electrically biased thermistor element, mounted proximate the tip of a liquid-aspirating probe, to determine that the probe is safely submerged within a body of liquid to be aspirated at all times during the aspiration process. Also disclosed are different aspiration probe assemblies that are useful in the method and apparatus of the invention.

6 Claims, 7 Drawing Sheets

CPU
18
22
16
10
19
14
12
20
12A
AM
S
F
V
L
C

METHOD AND APPARATUS FOR ASPIRATING LIQUID FROM A CONTAINER

BACKGROUND OF THE INVENTION

1. Field of the Invention

The present invention relates to improvements in methods and apparatus for aspirating a predetermined volume of liquid from a container (e.g., a test tube or vial) with an aspirating probe or needle. More particularly, it relates to improvements in methods and apparatus for assuring that the aspirating probe is safely positioned within the liquid sample during the entire liquid-aspirating process to avoid an unintentional introduction of air into the aspirated volume. The invention is particularly useful in the fields of hematology, fluorescence flow-cytometry and blood chemistry where it is often necessary to aspirate and dispense, with high precision, relatively minute volumes (of the order of microliters) of blood and liquid reagents used for the analysis of such blood.

2. Discussion of the Prior Art

Automated hematology instruments typically include apparatus for automatically aspirating a blood sample from a sealed test tube and for dispensing one or more precise aliquots of the aspirated sample to a workstation for processing. In such instruments, a hollow sample-aspirating needle is automatically advanced downwardly, usually along a vertical path coincident with the longitudinal axis of the blood-containing test tube. During such movement, the sharp distal end or tip of the aspirating needle punctures the septum that seals the tube, travels through a volume of air positioned between the sample and the septum, and eventually enters into the blood sample to be aspirated. Thereafter, a vacuum pump is activated for a predetermined time interval to aspirate a desired volume (e.g., 250 microliters) of sample into and through an internal lumen of the aspirating needle to which the vacuum pump is operatively connected by a suitable conduit. The aspirated sample is typically segmented (e.g., by a conventional blood-sampling valve of the type disclosed in the commonly owned U.S. Pat. No. 4,896,546 to Cabrera et al.) to provide a plurality of relatively small aliquots (each being between about 5 and 75 microliters) which are then dispensed and mixed with suitable reagents in which the sample aliquots are analyzed. Alternatively, the aspirated sample can also be segmented by means of a positive-displacement (syringe-type) pump in a system in which the aspirating probe also functions as a dispensing probe.

In blood-aspirating apparatus of the above type, it will be appreciated that the preciseness of the sample volume aspirated requires that the probe tip be completely submerged in the blood sample at all times during the aspiration process. Should the aspirating vacuum force be applied to the probe for a period of time while the probe tip is positioned outside the sample volume, e.g., within the air pocket above the sample, air will be drawn into the probe, and the precision of the aspiration will be compromised. This condition is exacerbated in a sample aspirate/dispense system of the above-mentioned type since such a "suck and spit" system does lend itself to the use of an in-line bubble detector. Various schemes have been proposed and used to date for avoiding the aspiration of air into the sample line. For example:

In the commonly owned U.S. Pat. No. 4,341,736 to Drbal et al., a fluid (i.e., liquid) transfer mechanism is disclosed for aspirating biological fluid samples from a series of open cuvettes or containers. This patent discloses two different schemes for signaling that the tip of a fluid-aspirating probe is safely submerged within a fluid sample so that aspiration can occur without drawing air into the aspirated sample. Both schemes make use of the electrical properties of the fluid sample in generating the signal. According to a first scheme, the probe is constructed from a non-conductive plastic tube. The tube supports a pair of spaced, parallel electrodes that run along the entire tube interior and terminate at the aspirating end of the tube. The opposite ends of the electrodes are connected across an electrical power supply. As the electrode ends on the probe tip move towards and eventually contact the sample fluid, an electrical circuit is completed through the sample fluid; thus, a signal is produced indicating that the probe tip has now entered the sample fluid and aspiration can safely occur. According to the second scheme, the aspirating probe is made of stainless steel, and the sample fluid is contained either in an electrically conductive container, or if the container is non-conductive, the container is supported on a conductive base. The steel probe is electrically connected to an AC power source, and the conductive container or base is electrically grounded. As the probe tip moves towards and eventually contacts the surface of the sample fluid, a change in electrical capacitance occurs between the probe tip and container (or base), as determined by the dielectric properties of the intervening sample fluid. This capacitance change is detected in a bridge circuit that signals that the probe has contacted and entered the sample fluid.

In using liquid level-sensing apparatus of the type noted above, a problem can arise when the liquid sample to be aspirated is subject to foaming when agitated. In the field of hematology, it is common to continuously rock, and thereby agitate, a blood sample in a test tube to assure, for example, the homogeneity of the sample during analysis. The continuous movement of the blood forward and backward in the vial can eventually lead to the formation of a bubbly mixture of air and blood (i.e., foam) on the surface of the sample. Unfortunately, the electrical properties of the foam differs little from the sample itself. Thus, in the above apparatus, as soon as the electrodes or conductive aspirating probe contacts the foam, a signal is generated indicating that the probe is in a position ready for sample aspiration. When this occurs, air bubbles can be drawn into the aspirated sample, thereby making the aspirated volume uncertain. Further, in liquid level sensors of the capacitance level-sensing type, it is usually necessary to maintain the test tube (when it is non-conductive) in a generally upright orientation at all times. This orientation assures that the counter electrode (the conductive base on which the test tube rests) is in close proximity to the sample liquid. Thus, this liquid level-sensing scheme is not useful in instruments in which the test-tube is inverted (with its seal facing downward) during sample aspiration.

SUMMARY OF THE INVENTION

In view of the foregoing discussion, an object of the present invention is to provide an improved liquid-aspirating method and apparatus for aspirating liquid from a container with a liquid-aspirating probe.

Another object of this invention is to provide a liquid-aspirating apparatus of the type described that is capable of distinguishing a layer of foam or bubbles atop a liquid surface from the underlying liquid itself in a container.

Another object of the invention is to provide an improved liquid-aspirating probe assembly that is adapted for use in an apparatus for sensing the submersion of the tip of an aspiration probe in a liquid sample to be aspirated.

According to a first aspect of the invention, a method for aspirating a liquid from a container comprises the steps of (a) mounting a thermistor proximate the tip of a liquid-aspirating probe, (b) applying a predetermined constant current to the thermistor to cause the temperature of the thermistor to rise to a predetermined level higher than the ambient temperature surrounding the thermistor, (c) advancing the probe tip towards and into the liquid to be aspirated while sensing the resistance of the thermistor, and (d) applying a vacuum force to the aspirating probe to cause liquid to be aspirated into the probe upon sensing that the thermistor resistance indicates that the thermistor has passed through any foam atop the liquid to be aspirated and has entered the body of liquid to be aspirated.

According to a second aspect of the invention, a new and improved liquid-aspirating apparatus comprises a liquid-aspirating probe supporting a thermistor element proximate its distal, liquid-aspirating end. A bias circuit operates to heat the thermistor to a level above ambient (room temperature), while a bridge circuit or the like operates to monitor the thermistor temperature and heat loss occasioned by the movement of the distal end of the probe into a liquid sample to be aspirated. A control circuit is responsive to the output of the second circuit to apply a vacuum force to the probe to aspirate liquid therein.

According to a third aspect of the invention, new and improved liquid-aspirating probe assemblies are provided. Such assemblies comprise an elongated cylindrical aspiration probe, e.g., a cannula, preferably having a sharpened distal end that is adapted to pierce seals on liquid sample containers, and a thermistor mounted on the probe proximate its distal end. According a first embodiment, the probe has internal walls that define at least a pair of elongated channels or lumens that extend generally parallel to the probe axis, terminating in the vicinity of the distal tip of the probe. One lumen is used to aspirate liquid through the probe, and the other lumen is used to contain the electrical lead(s) by which the thermistor, mounted within such other lumen in the vicinity of the probe tip, can be connected to a remotely located control circuit that serves to both heat the thermistor to a desired initial temperature, as well as to monitor the thermistor temperature, as reflected by its instantaneous resistance, as the probe tip moves towards a liquid volume to be aspirated. According to a second embodiment, the thermistor leads are contained within an elongated groove or channel formed in the exterior wall of the probe and extending parallel to the probe's longitudinal axis.

The invention and its advantages will be better understood from the ensuing detailed description of preferred embodiments, reference being made to the accompanying drawings in which like reference characters denote like parts.

DETAILED DESCRIPTION OF PREFERRED EMBODIMENTS

Figure 1:
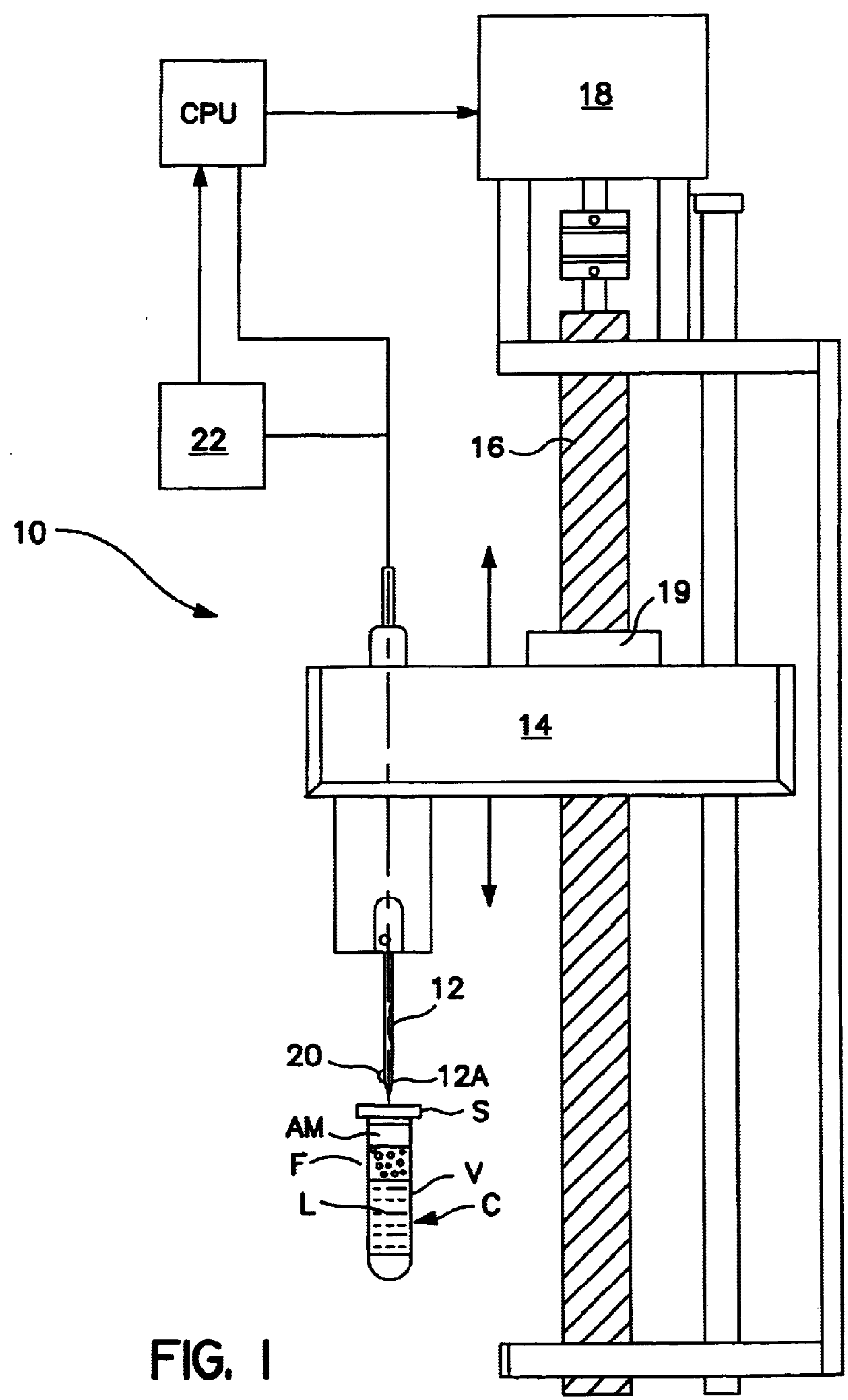
FIG. 1 illustrates a liquid-aspirating apparatus embodying the invention.

Referring now to the drawings, FIG. 1 illustrates a liquid-aspirating apparatus 10 for aspirating a liquid L, such as whole blood, from a container C. The container may be in the form of a sealed test tube or vial V, as shown, or in the form of an open cuvette. Apparatus 10 comprises an aspirating probe 12, e.g., a hollow needle or cannula that is supported for vertical movement by a movably-mounted carriage 14. The latter is operatively coupled, in a conventional manner, to a threaded lead screw 16 that is selectively rotated by a bi-directional stepper motor 18. As the threaded lead screw rotates, its rotational motion is translated to linear movement of the carriage by a threaded nut 19 carried by the carriage. Operation of the stepper motor is controlled by a suitably programmed microprocessor comprising a central processing unit CPU.

In accordance with the invention, probe 12 carries a conventional thermistor element 20 at its tip or distal end 12A. As described below, the thermistor is used as a liquid-level sensor for the purpose of assuring that the aspirating portion of the probe is safely submerged within the liquid sample L at all times during the aspiration process. A particularly preferred thermistor for this application is that made and sold by Thermometrics, Inc. under Part No. B10KA103K. Such a thermistor is encapsulated in a tiny glass bead having a diameter of about 0.010 inch (0.25 mm); it is adapted to operate at a power level up to 1/10 watt.

Prior to liquid aspiration, the thermistor element 20 is pre-heated by the application of a suitable electrical bias current to a temperature at which its internal resistance reflects a temperature somewhat higher, preferably about 5 to 10 degrees Fahrenheit higher, than the ambient room temperature. This electrical biasing renders the thermistor more sensitive to relatively small changes in temperature levels at or near room temperature, as is needed to reliably sense the submersion of the thermistor in a liquid at ambient (room) temperature. The thermistor bias current is provided by the output of the above-noted central processing unit. A bridge circuit 22 or the like serves to monitor changes in the thermistor temperature (i.e., its resistance), as occasioned by the liquid aspiration process. The manner in which the invention operates will be best appreciated by referring to FIG. 2.

Figure 2:
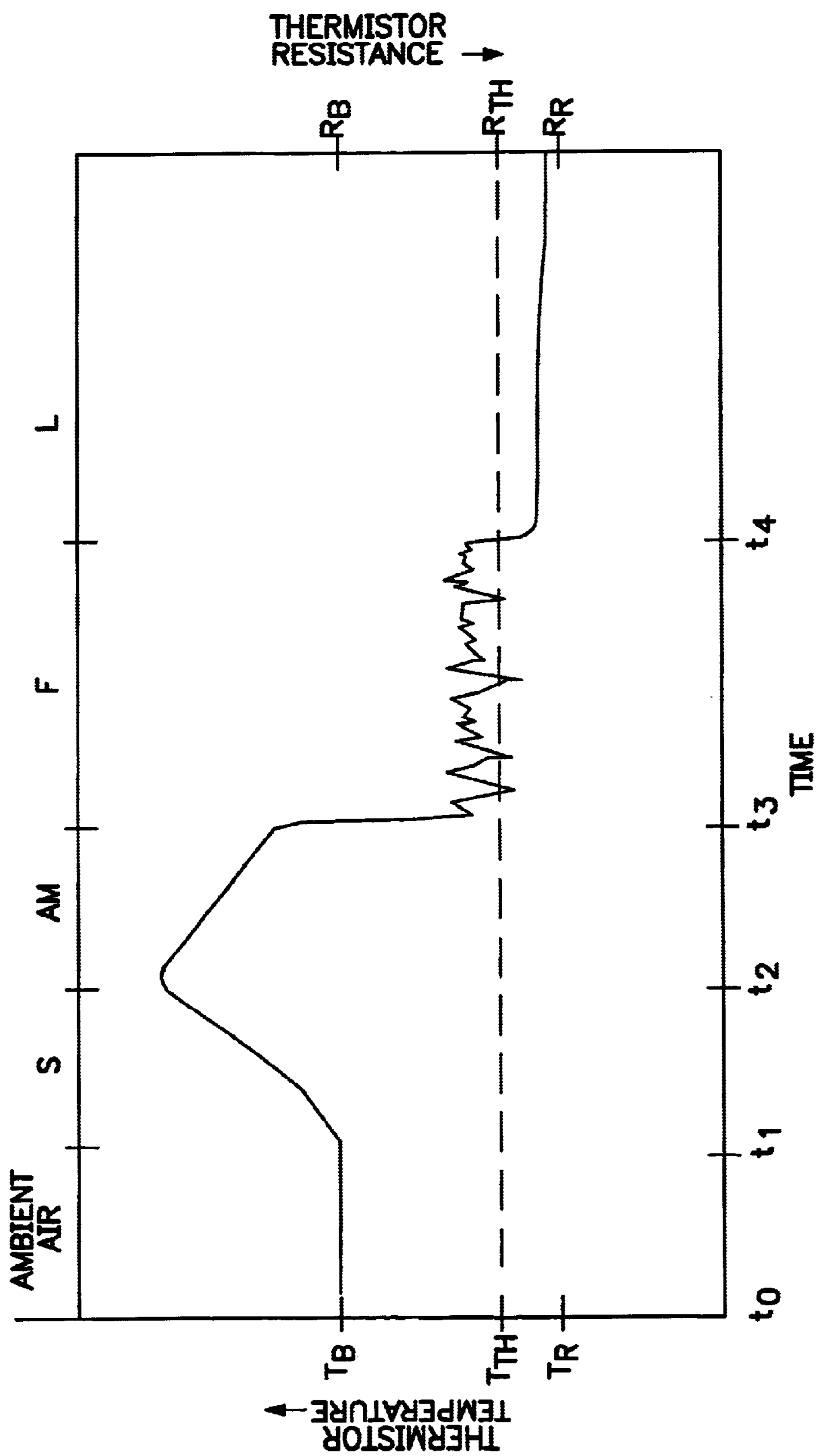
FIG. 2 is a graph illustrating changes in temperature and resistance of the liquid-sensing thermistor element used in the apparatus of FIG. 1.
Figure 6:
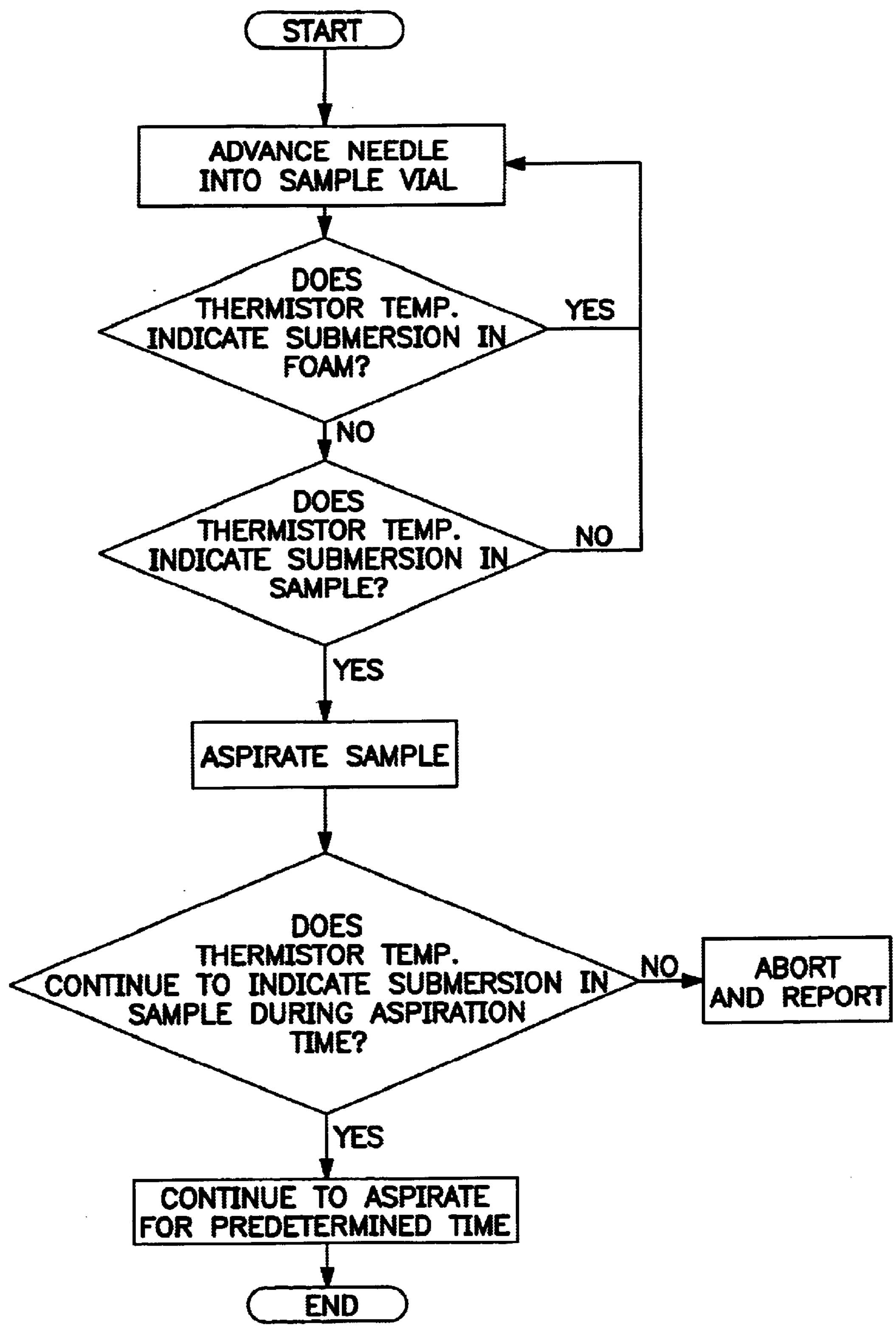
FIG. 6 is a flow chart illustrating a preferred program carried out by a microprocessor comprising the FIG. 1 apparatus.

In describing the operation of the invention, it is assumed that the liquid container is sealed by a rubber stopper S or the like, that the container is held in a vertically upright position, and that the aspiration probe is moved downward so that the tip thereof penetrates the stopper. However, from the ensuing description, it will be appreciated that the container need not be sealed for the inventive apparatus to operate, nor need the container be held vertically upright. Further, for the sake of illustration, it is assumed that the container is not completely filled, there being an air mass AM between the liquid and the bottom of the stopper, and that there is a layer of bubbles or foam F atop the liquid surface. Again, it will be appreciated that such an air mass need not be provided. Thus, as the tip of the aspirating probe moves downwardly from a position vertically above the liquid container, it first passes through the stopper S, then the air mass AM, then the foam layer F and finally enters the body of liquid L to be aspirated. Referring to FIG. 2, at time to, the thermistor temperature is set by the CPU at its initial bias temperature $T_B$, several degrees above room temperature $T_R$. At this time, the thermistor resistance, as determined by its temperature, will be at the bias level $R_B$. Note, as shown by the oppositely directed arrows on the right and left ordinates of the graph, the thermistor resistance is inversely proportional to its temperature; thus, as the temperature of the thermistor increases, its resistance decreases. At time $t_1$, the thermistor, as mounted proximate the tip of the downwardly-moving aspirating probe, enters and moves through the penetrable stopper S, and frictional forces presented by the dynamic stopper/thermistor interaction will cause the thermistor temperature to begin to rise above its initial bias temperature $T_B$. At time $t_2$, when the probe tip emerges from the stopper and enters the air mass AM above the liquid sample, the thermistor temperature will begin to return towards its initial bias temperature $T_B$, albeit at a relatively slow rate due to the relatively low heat-transfer characteristics of air. As the probe tip enters the foam layer F at time $t_3$, the thermistor temperature will suddenly drop and stabilize at a level determined by the heat-transfer characteristics of the foam. As shown, the thermistor temperature will rapidly and randomly vary while passing through the foam layer, and its instantaneous level will be determined by whether the thermistor is in an air pocket (bubble) or in the liquid forming the air pocket. When in a space primarily comprising air, the thermistor temperature will rise towards the bias level; conversely, when the thermistor is in a space primarily composed of liquid, the thermistor temperature will drop towards the temperature of the liquid (i.e., room temperature). At time $t_4$, the probe tip enters the liquid sample and, owing to the much higher thermal conductivity of the liquid (cf. to foam), the thermistor temperature drops relatively precipitously to a steady-state level between $T_B$ and $T_R$. Note, while the temperature of the liquid is room temperature, the bias current applied to the thermistor will cause it to indicate a somewhat higher temperature. Upon receiving an input from circuit 22 that the thermistor temperature has remained at this steady state level for a predetermined time interval measured from time $t_4$, the CPU produces a signal causing a vacuum force to be applied to the probe, whereby liquid aspiration begins. In the event that the thermistor temperature (as reflected by the thermistor resistance) begins to increase during aspiration, thereby indicating that the thermistor is no longer submerged in the liquid sample, an abort signal is generated by the CPU and the aspirated sample is discarded. This event may occur when either the level of liquid in the container has dropped below that required for aspirating the volume of liquid desired, or there has been relative movement between the container and probe during aspiration. The flow chart of FIG. 6 illustrates the program carried out by the system's microprocessor in implementing the above-described series of steps.

Figure 3:
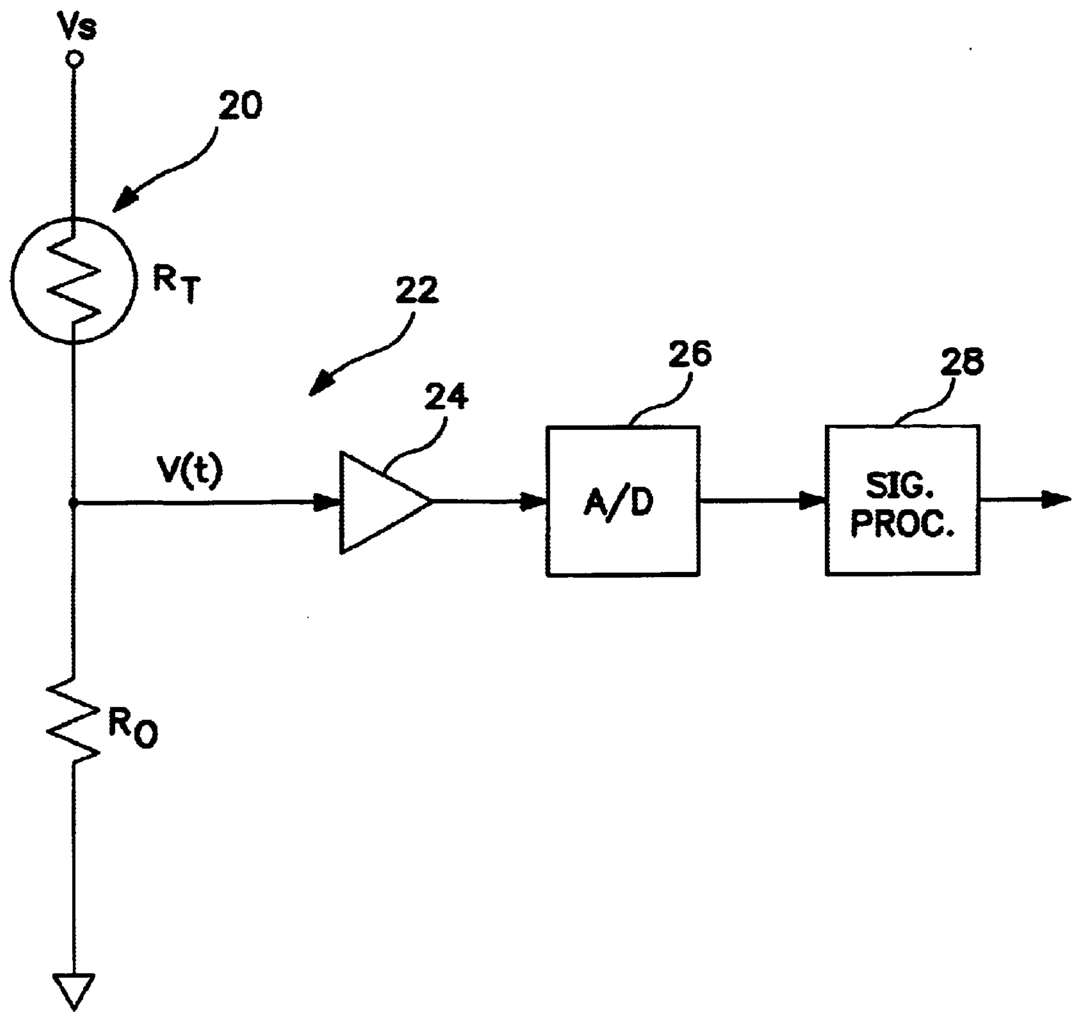
FIG. 3 is an electrical schematic drawing of a preferred control circuit for processing an electrical signal resulting from changes in the resistance of a thermistor.

In FIG. 3, a preferred control circuit 22 is shown for monitoring the thermistor temperature and for providing a signal by which the position of the aspiration probe can be controlled. Circuit 22 includes a voltage divider network, comprising resistor $R_0$ and the thermistor resistance $R_T$, that is driven by a DC voltage source $V_S$. The output V(t) of the voltage divider network is amplified and filtered by an amplifier circuit 24 which serves to amplify the input signal to levels compatible with the input signal range of an analog-to-digital circuit 26. The filter circuit within amplifier 24 eliminates unwanted, spurious signals outside a desired frequency spectrum. The digital output of circuit 26 is processed by the digital signal processing circuit 28 using a software algorithm resident therein. The function of the algorithm is to provide a first output flag (1) to the CPU when the waveform pattern of V(t) indicates that the thermistor is in contact with either air or foam, in which case the thermistor resistance TR is above a threshold level $R_{TH}$ and/or that the signal is rapidly varying and unstable. When the thermistor is submerged in liquid, the software algorithm provides a second flag (0) to the CPU, indicating that the stepper motor has moved the aspirating port of the aspiration probe sufficiently far into the liquid vial that aspiration can be safely initiated. Preferably, the criteria used to discriminate foam from liquid are based on the amplitude of the fluctuations of F(t).

Figure 4A:
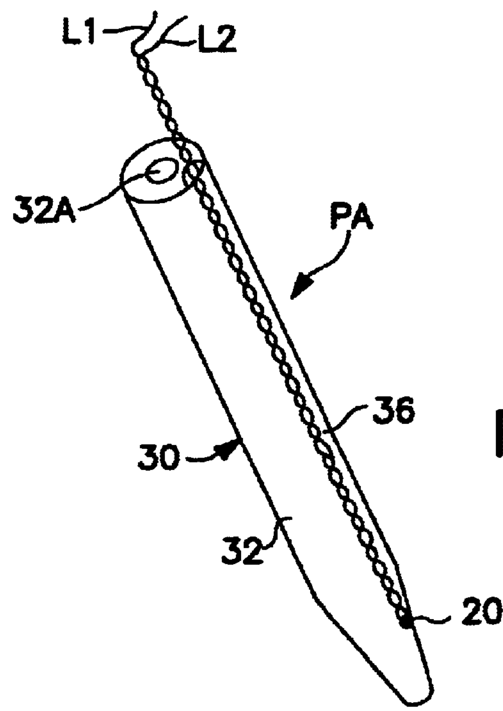
FIGS. 4A, 4B and 4C are enlarged perspective, side and cross-sectional illustrations, respectively, of a first preferred liquid-aspirating probe assembly structured in accordance with the present invention.
Figure 4B:
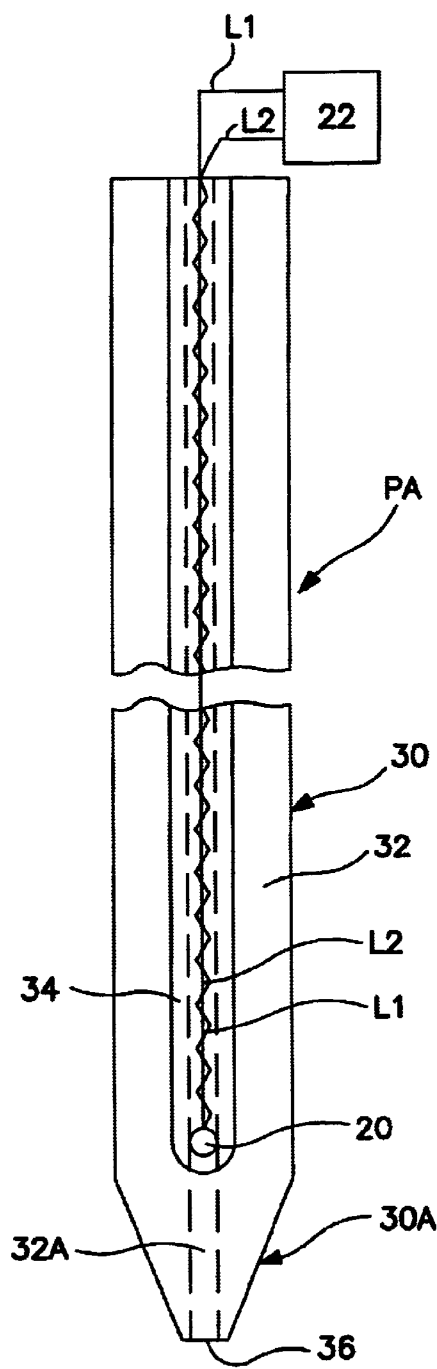
Figure 4C:
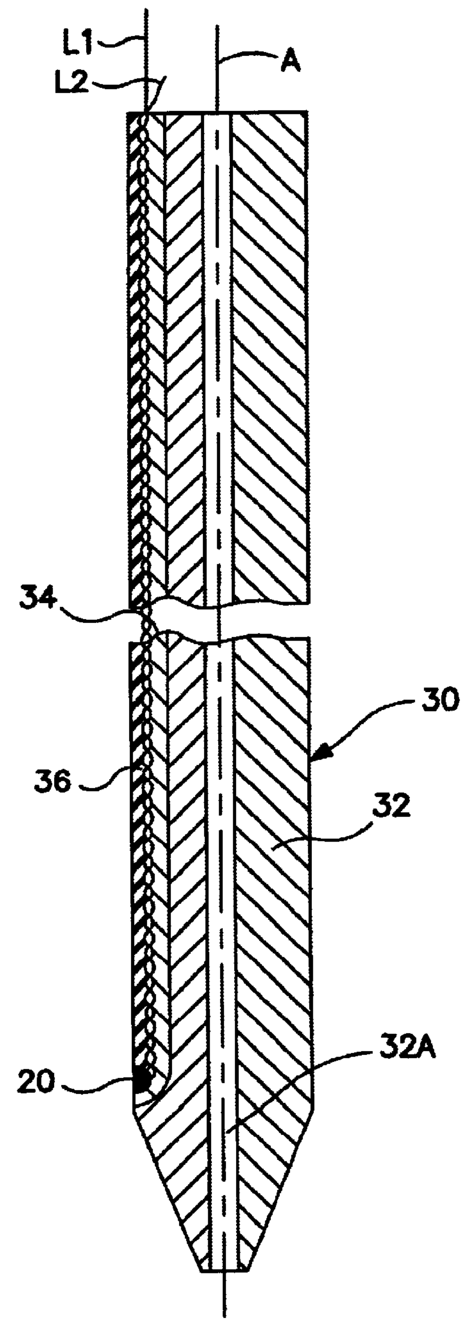

Referring to FIGS. 4A–4C, a preferred liquid-aspirating probe assembly PA is shown to include a cannula 30 comprising a tubular housing 32, and a thermistor element 20 mounted in close proximity to the cannula's distal end 30A. Tubular housing 32 is preferably made of stainless steel, and its outside diameter is preferably between about 1.0 and 2.0 mm. Tubular housing 32 defines a central bore hole or lumen 32A of about 0.20 mm. in diameter that extends axially along the entire length of the housing. Thus, the wall of housing 32 has a thickness between about 0.4 mm and 0.9 mm. Liquid is aspirated through the central lumen when a vacuum is applied thereto and its distal end 36 is submerged in liquid. The outer wall of housing 32 defines an elongated groove or channel 34 extending parallel to the tube axis A. The depth of channel 34 is preferably about 0.375 mm, and its transverse cross-section is shaped to receive a pair of electrical leads L1,L2 by which thermistor 20 is connectable to the remotely positioned bias and temperature-monitoring circuit 22. The thermistor element 20 is arranged at the distal end of channel 34; this corresponds to an axial location slightly above the tapered portion 30A of the cannula. Being located vertically above the aspiration port of the cannula, the aspiration port will always be submerged in the liquid when the thermistor temperature indicates that the thermistor is submerged in the liquid. The thermistor and its leads are held in channel 34 by a suitable epoxy adhesive 36 that extends along the entire length of channel 34.

Figure 5A:
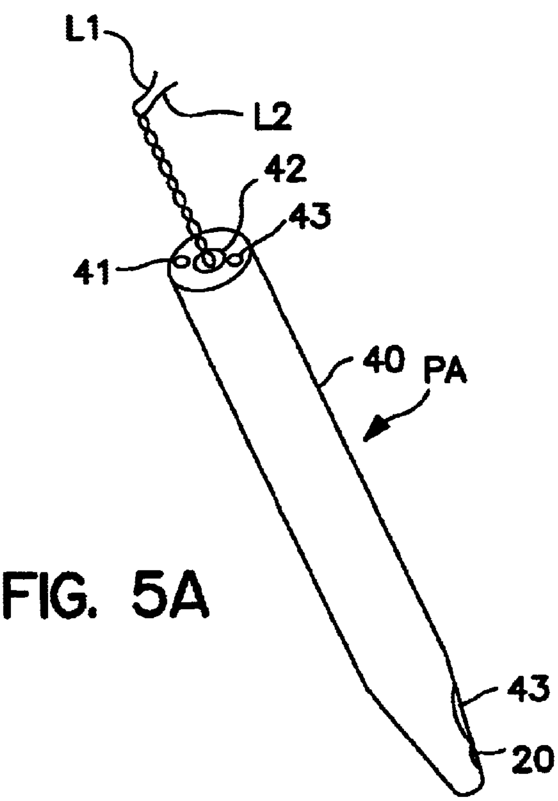
FIGS. 5A, 5B and 5C are enlarged perspective, side and cross-sectional illustrations, respectively, of a second preferred liquid-aspirating probe assembly structured in accordance with the present invention.
Figure 5B:
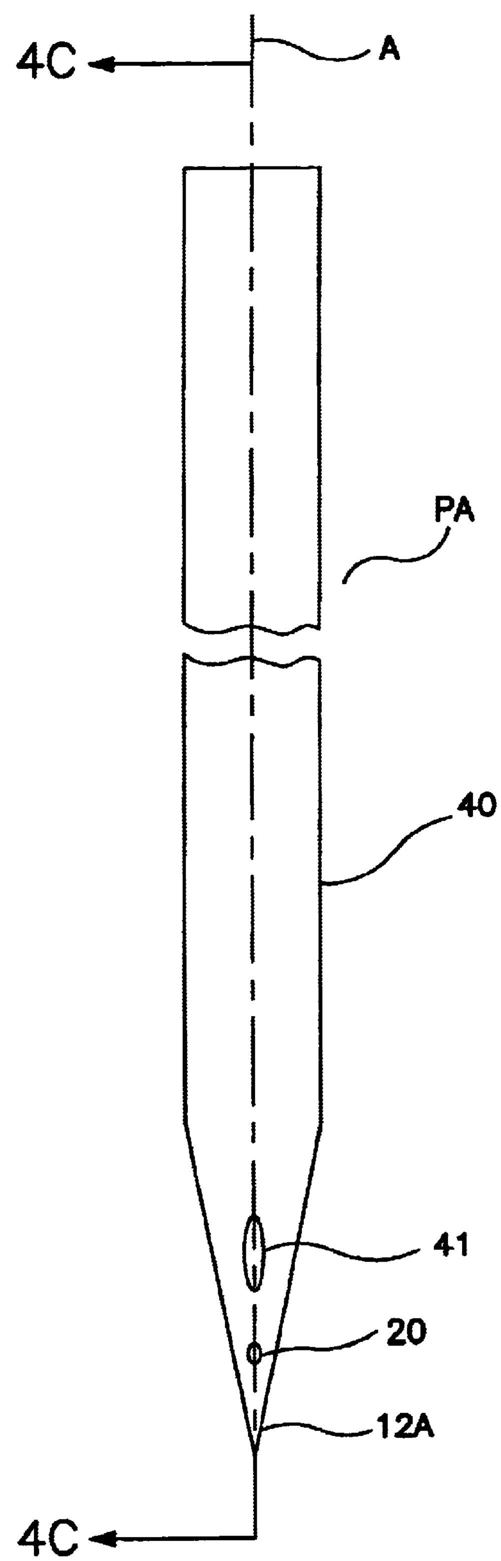
Figure 5C:
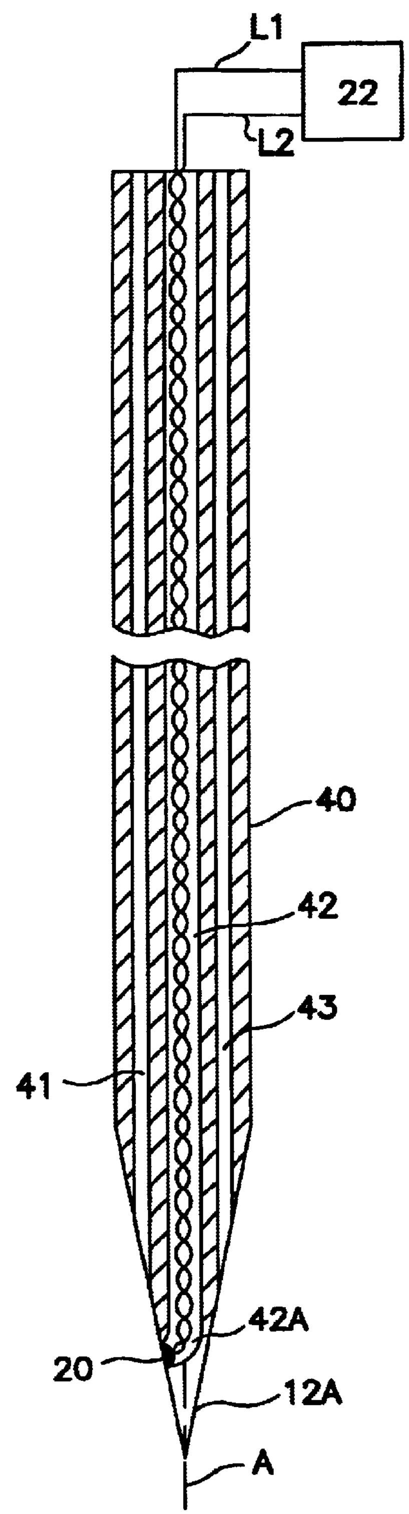

FIGS. 5A–5C illustrate another preferred embodiment of the probe assembly PA. Here, the probe assembly comprises a stainless steel cannula 40 having three internal lumens 41, 42, and 43 formed therein. The outboard lumens 41 and 43 serve, respectively, to aspirate liquid and to vent the container (in the event the container is sealed). The central lumen 42 is concentric with the cannula axis A over most of its length, and is used to house the thermistor leads L1, L2 used to bias and detect temperature changes in the thermistor element 20. A small angularly-directed channel 42A allows channel 42 to communicate with the exterior of the probe, and the thermistor 20 is affixed at the external surface of the probe using a suitable epoxy material.

While the invention has been described with reference to particularly preferred embodiments, it will be apparent that changes can be made without departing from the spirit of the invention. Such changes are intended to fall within the scope of the appended claims.

What is claimed is:

1. In a method for analyzing a blood sample, a method for aspirating a volume of blood from a container comprising the steps of:

(a) mounting a thermistor proximate the tip of a blood-aspirating probe;

(b) applying a predetermined constant current to the thermistor to maintain the temperature of the thermistor at an initial predetermined level higher than the ambient temperature surrounding the thermistor;

(c) advancing the probe tip towards and into the blood to be aspirated while monitoring the resistance of the thermistor; and (d) applying a vacuum force to the aspirating probe to cause blood to be aspirated into the probe upon sensing that the thermistor resistance has risen above a preset threshold level, thereby indicating that the thermistor has entered the blood to be aspirated and that the thermistor temperature has dropped below a threshold level.

2. The method as defined by claim 1, wherein said applying step (d) is performed for a predetermined time interval or until said thermistor temperature rises above said threshold level, whichever occurs first.

3. The method as defined by claim 1 wherein said thermistor-mounting step (a) comprises the steps of (i) forming an axially-extending channel in the external wall of said liquid-aspirating probe, (ii) positioning said thermistor and a pair of electrical leads associated therewith within said channel, and (iii) bonding said thermistor and electrical leads within said channel with an adhesive.

4. The method as defined by claim 1 wherein said thermistor-mounting step (a) comprises the steps of (i) forming a substantially axially-extending lumen within said liquid-aspirating probe, said lumen communicating with the exterior of said probe in the vicinity of a distal end of said probe, affixing said thermistor in said lumen at a location where said lumen intersects the exterior of said probe, and positioning a pair of electrical leads associated with said thermistor within said lumen.

5. For use in an instrument adapted to analyze a blood sample, apparatus for aspirating a volume of blood from a container comprising:

(a) a blood-aspirating probe assembly comprising (i) a hollow probe having a tip through which blood can be aspirated into said probe; and (ii) a thermistor mounted proximate said tip of the blood-aspirating probe;

(b) a first electrical circuit for applying a predetermined constant current to said thermistor to maintain the temperature of the thermistor at an initial predetermined level higher than the ambient temperature surrounding the thermistor;

(c) a drive mechanism for selectively advancing the probe tip towards and into a body of blood within a container;

(d) a second circuit for monitoring the resistance of the thermistor; and (e) a central processing unit responsive to the second circuit for applying a vacuum force to the aspirating probe to cause blood to be aspirated into the probe upon sensing that the thermistor resistance has risen above a preset threshold level, thereby indicating that the thermistor has entered the blood to be aspirated and that the thermistor temperature has dropped below a threshold level.

6. A blood-aspirating probe assembly comprising:

(a) an aspiration probe adapted to enter a container of blood to aspirate a sample for analysis, said probe comprising a cylindrical housing; and (b) a thermistor element affixed to said probe housing in the vicinity of a distal end thereof, said thermistor element having at least one electrical lead connected thereto, said probe housing defining (i) a first axially-extending internal lumen having an opening located in the vicinity of said distal end of said probe housing through which a blood sample can be aspirated into said lumen upon inserting said opening into a volume of blood within said container and applying a vacuum force to said lumen; (ii) a second axially-extending lumen adapted to receive said thermistor lead and having an opening to the atmosphere in the vicinity of said distal end of said housing, said thermistor element being supported in said opening by an adhesive; and (iii) a third axially-extending lumen open to the atmosphere at both ends and adapted to vent a sealed blood-containing container to the atmosphere prior to aspiration of said blood sample.

* * * * *